(12) United States Patent
Khuzwayo

(10) Patent No.: US 8,770,048 B2
(45) Date of Patent: Jul. 8, 2014

(54) DEVICE FOR MEASURING AND SAMPLING LIQUID

(76) Inventor: Simphiwe Lionel Khuzwayo, Kempton Park (ZA)

( * ) Notice: Subject to any disclaimer, the term of this patent is extended or adjusted under 35 U.S.C. 154(b) by 295 days.

(21) Appl. No.: 13/511,537

(22) PCT Filed: Nov. 26, 2010

(86) PCT No.: PCT/IB2010/055444
§ 371 (c)(1),
(2), (4) Date: May 23, 2012

(87) PCT Pub. No.: WO2011/064746
PCT Pub. Date: Jun. 3, 2011

(65) Prior Publication Data
US 2013/0000391 A1    Jan. 3, 2013

(30) Foreign Application Priority Data

Nov. 26, 2009   (ZA) .................................. 2009/08360

(51) Int. Cl.
*G01N 1/10* (2006.01)
*G01N 1/16* (2006.01)

(52) U.S. Cl.
CPC ... *G01N 1/16* (2013.01); *G01N 1/10* (2013.01)
USPC .................. 73/863.71; 73/864.51; 73/864.63; 73/864.64

(58) Field of Classification Search
CPC .................................. G01N 1/10; G01N 1/16
USPC ........ 73/863, 863.71, 864.51, 864.63, 864.64
See application file for complete search history.

(56) References Cited

U.S. PATENT DOCUMENTS

| | | | | |
|---|---|---|---|---|
| 1,078,847 A | * | 11/1913 | Grauenfels et al. | 73/863.31 |
| 2,185,651 A | * | 1/1940 | Sollie | 73/864.64 |
| 2,208,682 A | * | 7/1940 | O'Brien | 91/52 |
| 2,822,783 A | * | 2/1958 | Clifton et al. | 137/625.12 |
| 3,080,760 A | * | 3/1963 | Piersma | 73/863.31 |
| 3,801,440 A | | 4/1974 | Rohrer, Jr. et al. | |
| 3,870,078 A | | 3/1975 | Apt, Jr. et al. | |
| 3,965,750 A | * | 6/1976 | Johnson | 73/864.51 |
| 4,088,025 A | * | 5/1978 | Foster et al. | 73/863.33 |
| 4,346,519 A | * | 8/1982 | Milo | 33/717 |
| 4,790,198 A | * | 12/1988 | Awtry et al. | 73/864.64 |
| 4,911,026 A | * | 3/1990 | Keives | 73/864.64 |
| 5,337,620 A | * | 8/1994 | Kalidini | 73/864.64 |

(Continued)

FOREIGN PATENT DOCUMENTS

GB             331726 A  *  7/1930

*Primary Examiner* — David A Rogers
(74) *Attorney, Agent, or Firm* — Ladas & Parry LLP

(57) ABSTRACT

The invention provides a liquid storage installation which includes a tank (70) containing a liquid and a device (10) for measuring and sampling the liquid. The device (10) includes an elongate hollow body (12) having a closed bottom and a plurality of spaced apart sampling ports (20, 22, 24) at spaced apart positions. The device (10) further includes a sleeve (14) which extends around the sampling port and in which corresponding sampling ports (26, 28, 30) are provided at spaced apart positions. The body (12) and sleeve (14) are displaceable relative to one another between an open position in which the sampling ports are in register permitting liquid flow between the tank and the interior of the body and a closed position in which the ports are out of register and flow between the tank and the interior of the body (12) is prohibited.

17 Claims, 2 Drawing Sheets

(56) References Cited

U.S. PATENT DOCUMENTS

| | | | |
|---|---|---|---|
| 5,440,941 A * | 8/1995 | Kalidindi | 73/864.64 |
| 5,476,017 A * | 12/1995 | Pinto et al. | 73/864.62 |
| 5,739,440 A * | 4/1998 | Diadelfo et al. | 73/864.63 |
| 6,065,355 A * | 5/2000 | Schultz | 73/864 |
| 6,094,999 A * | 8/2000 | DuBois | 73/864.64 |
| 6,339,966 B1 | 1/2002 | Kalidindi | |
| 6,393,926 B1 * | 5/2002 | Bowersox et al. | 73/864.64 |
| 7,000,491 B1 * | 2/2006 | Nunez | 73/864.64 |
| 7,472,614 B1 * | 1/2009 | Kalidindi | 73/864.64 |

* cited by examiner

DEVICE FOR MEASURING AND SAMPLING LIQUID

RELATED APPLICATION INFORMATION

This application is a 371 of International Application PCT/IB2010/055444 filed 26 Nov. 2010 entitled "Device for Measuring and Sampling Liquid", which was published in the English language on 26 Nov. 2011, with International Publication Number WO 2011/064746 A2, and which claims priority from South African Patent Application No. 2009/08360 filed on 26 Nov. 2009, the content of which is incorporated herein by reference.

THIS INVENTION relates to a device for measuring and sampling liquid in a closed container. It also relates to a liquid storage installation.

According to one aspect of the invention there is provided a device for measuring and sampling liquid in a closed container which include;
- an elongate hollow body, an operatively lower end of which is closed;
- a sleeve surrounding the body for at least part of its length, the sleeve and body being displaceable relative to one another between an open position and a closed position;
- a pair of longitudinally spaced apart seals defining an annular chamber between a radially outer surface of the body and a radially inner surface of the sleeve;
- a sampling port provided in the body and opening into the annular chamber;
- an outer sampling port which extends through the sleeve; and a port seal which is configured such that when the body and sleeve are in their open position, the sampling ports are connected in flow communication to permit fluid flow therebetween thereby connecting the interior of the body in flow communication with a body of liquid in a said closed container and when the body and sleeve are in their open position, flow communication between the sampling ports and hence between the interior of the body and the body of liquid is inhibited.

According to another aspect of the invention there is provided a device for measuring and sampling liquid in a closed container which device includes:
- an elongate hollow body, an operatively lower end of which is closed;
- at least two sampling ports provided in the body at spaced apart positions; and
- a closure arrangement configured simultaneously to open the ports to connect the interior of the body in flow communication with liquid contained in a said container and permit the liquid to enter the body and to close the ports to prevent the flow of liquid between the interior of the body and the container.

The closure arrangement may include a sleeve surrounding the body for at least part of its length and being displaceable relative to the body between an open position and a closed position and, associated with each sampling port, a pair of longitudinally spaced seals defining an annular chamber between a radially outer surface of the body and a radially inner surface of the sleeve into which chamber the associated sampling port opens, an outer sampling port which extends through the sleeve and a port seal which is configured such that when the body and sleeve are in their open position, the associated sampling ports are in flow communication to permit fluid flow therebetween thereby connecting the interior of the body in flow communication with a body of liquid in a said closed container and when the body and sleeve are in their open position, flow communication between the sampling ports and hence between the interior of the body and the body of liquid is inhibited.

The or each port seal may include a seal element surrounding one of the ports in the body and the sleeve and sealingly abutting against an opposed surface of the other of the body and the sleeve. When the body and sleeve are in their open position the sampling ports may be in register and connected in flow communication through the port seal.

The sleeve may have a slot provided therein, a lug attached to the body protrudes through the slot, the open and closed positions of the body and sleeve corresponding to the lug being positioned at opposite ends of the slot.

In one embodiment of the invention the slot may extend circumferentially, relative displacement of body and sleeve being effected by displacing them angularly relative to one another.

In another embodiment of the invention, the slot may extend longitudinally, relative displacement of the body and sleeve between their open and closed positions being achieved by relative axial displacement therebetween.

In yet another embodiment of the invention, the slot may extend at an angle or obliquely, relative displacement of the body and sleeve between their open and closed positions being achieved by both angular and longitudinal displacement relative to one another The device may include a status display configured to provide a visual indication as to whether the body and sleeve are in their open position or their closed position.

The device may include a partition arrangement provided in the body and dividing the body into a plurality of different sections, at least one sampling port opening into each section.

The partition arrangement may include a longitudinally extending partition which divides a cavity defined within the body into longitudinal sections into each of which at least one sampling port extends.

The partition arrangement may include a plurality of longitudinally spaced transverse partitions which divide a cavity defined within the body into longitudinally spaced sections into each of which at least one sampling port extends.

In a preferred embodiment of the invention, the body defines a circular cylindrical chamber, the partition arrangement including a longitudinally extending partition and at least two longitudinally spaced apart partitions which protrude from one side of the longitudinally extending partition such that on one side of the longitudinally extending partition the cavity is divided into longitudinally spaced apart sections into each of which a sampling port extends and on the other side of the longitudinally extending partition the cavity is divided into a longitudinal section which extends for the length of the longitudinally extending partition and into which a plurality of longitudinally spaced apart sampling ports extend.

The device may include an indicator means provided in the body and configured to provide an indication of the presence and nature of contamination in the liquid.

According to yet another aspect of the invention there is provided a device for measuring and sampling liquid in a closed container which device includes
- an elongate hollow body within which a liquid contained in a said closed container is receivable; and
- indicator means provided in the body and configured to prove an indication of the presence and nature of contamination in the liquid.

When liquid contained in the container is a liquid fuel, the indicator means may include a water indicator element which has a density which is greater than the density of the fuel and less than the density of water.

The indicator means may include a metal particle indicator comprising a buoyant member, at least part of which is magnetic to attract metal particles contaminating the liquid.

The indicator means may include a viscosity indicator element.

According to yet another aspect of the invention there is provided a liquid storage installation which includes
at least one tank in which liquid is receivable; and
at least one device of the type described above, mounted on the tank to measure and sample liquid contained in the tank.

The tank may be a subterranean tank and the liquid may be a liquid fuel.

The body of the device may be provided with markings which when read in conjunction with the level of liquid in the body provide an indication of the volume of liquid in the tank.

The invention will now be described, by way of example, with reference to the accompanying diagrammatic drawings.

Figure 1:
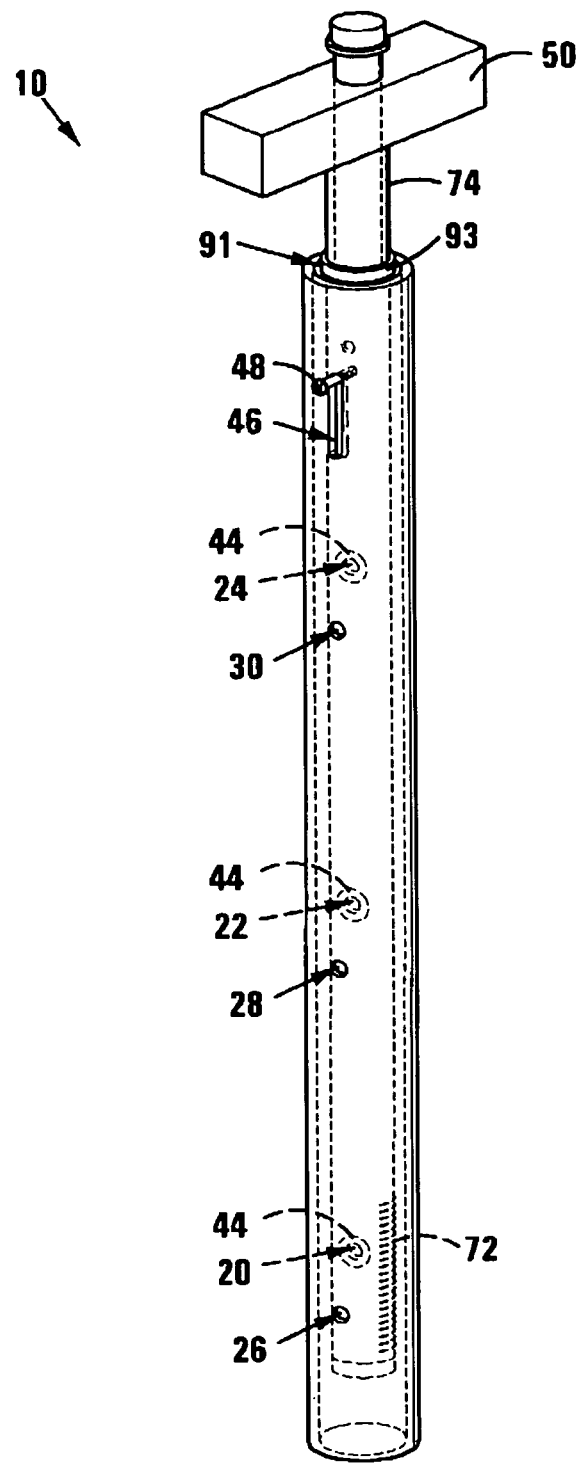
FIG. 1 shows a three-dimensional view of a device for measuring and sampling liquid in a closed container in accordance with the invention.

In the drawings, reference numeral 10 refers generally to device for measuring and sampling a liquid in a closed container in accordance with the invention.

The device 10 includes an elongate hollow body 12 and a sleeve 14 which surrounds the body 12 for at least a major part of its length.

The body 12 is formed from an elongate tubular member 16 of a synthetic plastics material such as a clear PVC. A plug 18 is provided in an operatively lower end of the tubular member 16 in order to close it.

The sleeve 14 is formed from a length of synthetic plastics tubing material such as a clear PVC and is dimensioned such that the inner diameter of the sleeve 14 is greater than the outer diameter of the member 16 such that a radial clearance 17 is provided therebetween.

Three longitudinally spaced apart pairs of sampling ports 20, 22 and 24 extend through the tubular member 16. The ports 20, 22, 24 in each pair are at diametrically opposed positions. Three corresponding pairs of outer sampling ports 26, 28 and 30 extend through the sleeve 14. Once again the ports 26, 28, 30 in each pair are at diametrically opposed positions.

Three pairs of longitudinally spaced apart seals 32, 34 and 36 define annular chambers 38, 40 and 42, respectively. Each pair of seals 32, 34, 36 includes two longitudinally spaced O-rings which sealingly abut the radially outer face of the tubular member 16 and radially inner surface of the sleeve 14. The pairs of sampling ports 20, 26; 22, 28 and 24, 30 open respectively into the chambers 38, 40 and 42.

A port seal 44 is associated with each sampling port 20, 22, 24. The port seal 44 extends around the sampling port and abuts sealingly against a radially inner surface of the sleeve 14 and the outer surface of the member 16.

It will accordingly be appreciated that the pairs of sampling ports 20, 26; 22, 28 and 24, 30 are connected in flow communication only when in register such that flow occurs through the associated port seal 44. This corresponds to the open position of the sleeve and body shown in FIG. 3.

In the embodiment shown, an elongate longitudinally extending slot 46 is provided in the sleeve 14. A guide element or lug formed by a screw 48 protrudes from the body 12 through the slot 46 and permits limited relative displacement between the body 12 and sleeve 14 between their open and closed positions which correspond to the lug being positioned at opposite ends of the slot 46 as shown respectively in FIGS. 2 and 3 of the drawings. Instead of extending longitudinally, the slot 46 could extend circumferentially so that relative displacement of the body 12 and sleeve 14 between their open and closed positions is effected by angular relative displacement. In another embodiment, the slot may extend obliquely such that the relative displacement between the body 12 and sleeve 14 has both an angular and an axial or longitudinal component.

A vent opening 49 extends through the tubular member 16 towards the upper end thereof. Optionally, a corresponding vent opening (not shown) can be provided in the sleeve 14 and a vent opening seal (not shown) similar to the port seal 44 can be provided so that the vent opening 49 is open to atmosphere, only when the body 12 and sleeve 14 are in their open position.

Displacement of the body 12 relative to the sleeve 14 is achieved by means of a handle 50 attached to an operatively upper end of the body 12.

A partition arrangement generally indicated by reference numeral 52 is provided in the body 12. The partition arrangement 52 includes a longitudinal partition 53 which separates the circular cylindrical cavity within the body 12 into two longitudinally extending semi-circular halves 54, 56. The partition arrangement 52 includes two longitudinally spaced apart partitions 55, 57 which protrude from one side of the partition 53 and divide the half 56 into three longitudinally spaced sections, namely a lower section 59, an intermediate section 61 and an upper section 63. One of the ports 20, 22, 24 in each pair opens into the half 54 at longitudinally spaced apart positions. The other ports 20, 22, 24 in each of the pairs open respectively into the lower section 59, intermediate section 61 immediately above the partition 55 and upper section 63 immediately above the partition 57, respectively. If desired, suitable seals can be provided between the edges of the partitions and inner surfaces of the body 12.

The device 10 includes indicator means 58 to provide an indication of the presence and nature of contamination in a liquid contained in a tank. The indicator means 58 includes, contained within the half 54 three spherical indicators 60, 62, 64. The indicator 60 is intended to provide an indication as to whether or not the fuel is contaminated with water. Accordingly, the indicator 60 has a density which is greater than that of the liquid, typically a liquid fuel which is to be measured and less than that of water. The indicator 64 is intended to provide an indication as to whether or not the liquid is contaminated with any metal particles. The indicator 64 accordingly includes a buoyant body to which a magnet is attached in order to attract metal particles contained within the liquid.

The indicator 62 is intended to provide an indication of the relative viscosity of the liquid. The indicator 62 includes a sealed body containing a sample of the liquid with which the device 10 is intended to be used in order to provide an indication of variations in the viscosity of the liquid as described in more detail herebelow.

The device 10 includes a status display, generally indicated by reference numeral 91 to provide a visual indication as to whether the body 12 and sleeve 14 are in their open position or their closed position. In this particular embodiment, the status display 91 includes an annular band 93 which is provided on the body 12 towards an upper end thereof. The band 93 is positioned such that when the body 12 and sleeve 14 are in their closed position the band is positioned above the upper edge of the sleeve 14 and is visible thereby indicating that the body 12 and sleeve 14 are in their closed position. However, as indicated in FIG. 3, when the body 12 and sleeve 14 are in their open position, the band 93 is located within the sleeve 14 thereby indicating that the body 12 and sleeve 14 are in their open position.

Figures 2, 3:
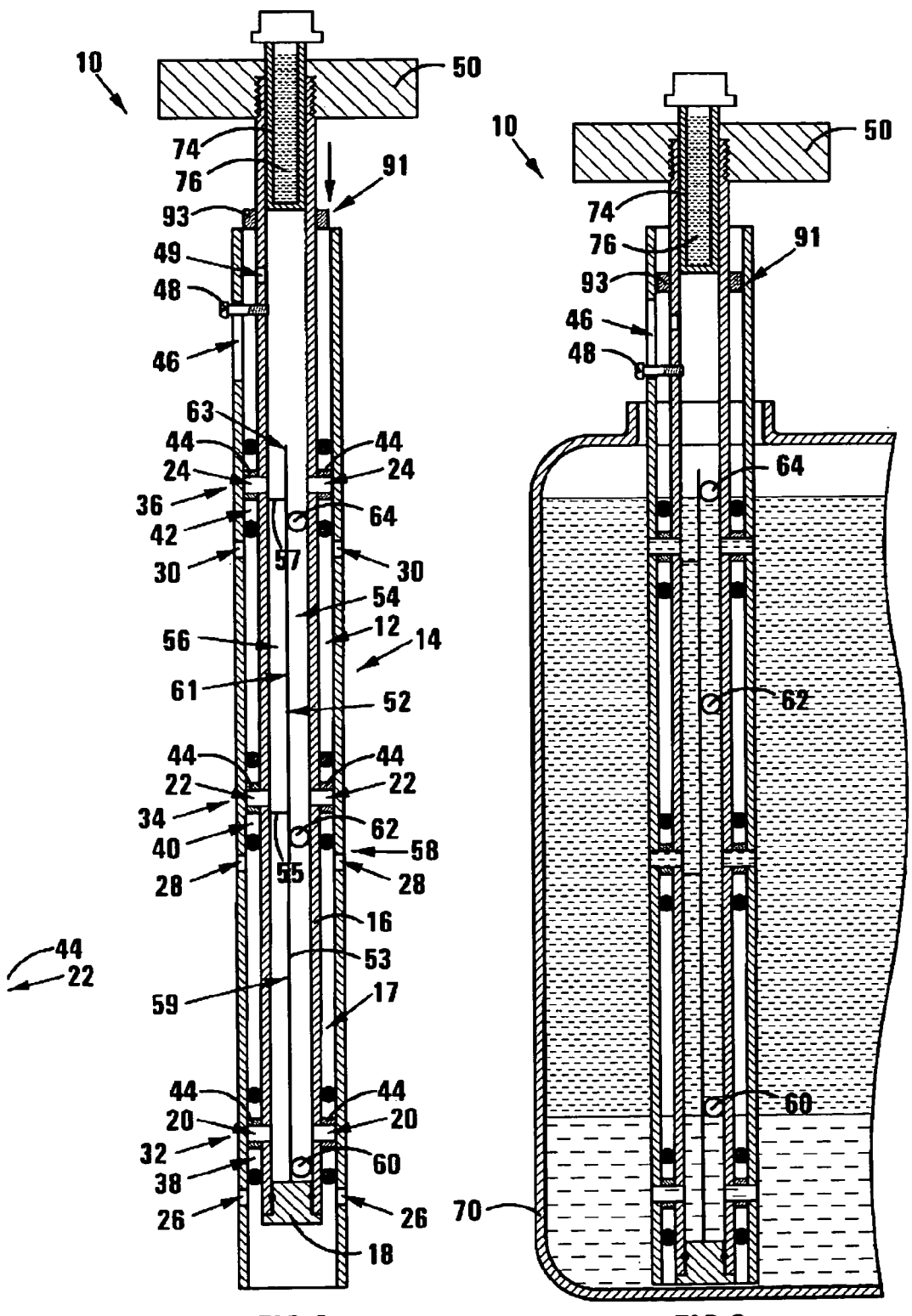
FIG. 2 shows an axial sectional elevation of the device of FIG. 1 in a closed position.
FIG. 3 shows an axial sectional elevation, similar to FIG. 2, of the device in its open position.

The device 10 typically forms part of an installation which includes a tank 70 part of which is shown in FIG. 3 of the drawings. The tank 70 contains a liquid such as a liquid fuel. Typically the tank 70 will be a subterranean tank positioned in a filling station.

In use the device 10 is positioned in the tank 70 such that a lower end of the body 12 is in abutment with or close to the bottom of the tank 70. The body 12 and sleeve 14 will normally be in their open condition (FIG. 3) in which liquid fuel contained within the tank 70 can enter the body 12 through the pairs of sampling ports 20, 26, 22, 28, 24, 30. It will be appreciated that, by virtue of the longitudinal spacing of the pairs of sampling ports, the strata of liquid contained within the body 12 will correspond to or closely approximate the strata contained within the body of liquid contained in the tank 70. More particularly, the partitions 55, 57 serve to separate the strata contained within the body and inhibit mixing thereby providing a more accurate indication of the strata contained within the body of liquid.

When it is desired to take a sample and measure the volume of liquid contained in the tank 10, the body 12 and sleeve 14 are displaced longitudinally relative to one another using the handle 50 so that the sampling ports 20, 22, 24, are out of register with the sampling ports 26, 28, 30 thereby effectively sealing the sampling ports 20, 22, 24 and retaining the fuel within the body 12.

The device 10 can then be raised and the level of liquid contained within the body 12 can be compared with markings 72 provided on the body 12 which provide an indication of the volume of liquid contained within the tank 70. It will be appreciated, that the markings 72 can be configured in order to take into account the geometry of the tank such that the level of liquid contained within the body 12 can provide a fairly accurate indication of the volume of liquid remaining in the tank.

By virtue of its density, if there is no water in the liquid, the indicator 60 will rest at the bottom of the body 12. If, however, there is water in the fuel, then the indicator 60 will float at the interface between the water and the fuel, as shown in FIG. 3, thereby providing an indication not only of the fact that there is in fact contamination of the fuel with water but also an indication of the volume of water contained within the tank.

Further, if metal particles are present in the fuel, e.g. as a result of corrosion within the tank, then the metal particles will be attracted to the indicator 64 to provide a visual indication of the contamination of the fuel.

As mentioned above, the indicator 62 contains the fuel contained within the tank and its buoyancy is selected such that when the fuel contained within the tank is at a desired viscosity, the indicator 62 will float within a predetermined range which is demarcated by suitable markings on the body 12 and/or sleeve 14. However, indicator 62 is floating at a position outside the desired zone, this is an indication that the viscosity of the fuel contained within the tank is outside desired parameters permitting remedial action to be taken.

If desired, a sealed container 74 can form part of the device 10 and can contain a sample 76 of the fuel or other liquid contained within the tank 70. This permits a visual comparison between the sample fuel 76 contained within the container 74 and that contained within the body 12 to ensure consistency.

Once the desired information has been obtained, the device 10 is once again lowered into the tank and the body 12 and sleeve 14 displaced to their open position in which fuel can flow freely between the interior of the body 12 and the body of fuel in the tank 70 and the level of fuel within the body 12 will vary corresponding with the level of fuel in the tank 70.

In order to reduce the risk of a build-up of static electricity, either a suitable anti-static material may be used in the manufacture of the device 10 or suitable earthing strips can be provided therein.

Currently, the level of fuel contained within a subterranean tank is measured by making use of a wooden dipstick. One disadvantage of using a wooden dipstick is that the demarcations on the dipstick through time become extremely difficult to read. This is both as a result of the staining of the wood by the liquid fuel as well as the marking becoming faint both as a result of use and exposure to the fuel. In addition, the liquid fuel evaporates relatively quickly from the surface of the dipstick making it difficult to obtain an accurate reading. In addition, during inclement weather conditions, it is extremely difficult to obtain an accurate reading since the wood becomes wet making it very difficult to ascertain the level of the liquid fuel marking on the dipstick. In addition the dipstick does not provide an indication of the presence or nature of contamination of the liquid fuel The Inventor believes that a device 10 in accordance with the invention will provide a cost effective and reliable manner of monitoring the level and quality of fuel contained within a subterranean tank and of providing an indication of the pressure and nature of contamination.

The invention claimed is:

1. A device for measuring and sampling liquid in a closed container, the device including:
an elongate hollow body, an operatively lower end of which is closed; at least two sampling ports provided in the body at spaced apart positions;
a closure arrangement configured simultaneously to open the ports to connect the interior of the body in flow communication with liquid contained in a said container and permit the liquid to enter the body and to close the ports to prevent the flow of liquid between the interior of the body and the container, wherein the closure arrangement includes:
a sleeve surrounding the body for at least part of its length and being displaceable relative to the body between an open position and a closed position;
associated with each sampling port, a pair of longitudinally spaced seals defining an annular chamber between a radially outer surface of the body and a radially inner surface of the sleeve into which chamber the associated sampling port opens;
an outer sampling port which extends through the sleeve; and
a port seal which is configured such that when the body and sleeve are in their open position, the associated sampling ports are in flow communication to permit fluid flow therebetween thereby connecting the interior of the body in flow communication with a body of liquid in a said closed container to permit liquid to enter the body and when the body and sleeve are in their closed position, flow communication between the sampling ports and hence between the interior of the body and the body of liquid is inhibited thereby retaining the liquid within the body; and a partition arrangement provided in the body and dividing the body into a plurality of different sections, at least one sampling port opening into each section, wherein the partition arrangement includes a longitudinally extending partition which divides a cavity defined within the body into two longitudinal sections into each of which at least one sampling port extends.

2. A device as claimed in claim 1, in which the partition arrangement includes a plurality of longitudinally spaced transverse partitions which divide one longitudinal section of the cavity into longitudinally spaced sections into each of which at least one sampling port extends.

3. A device as claimed in claim 1, in which the cavity defined within the body is a circular cylindrical chamber, the partition arrangement including at least two longitudinally spaced apart partitions which protrude from one side of the longitudinally extending partition such that on one side of the longitudinally extending partition the cavity is divided into longitudinally spaced apart sections into each of which a sampling port extends and on the other side of the longitudinally extending partition the cavity is divided into a longitudinal section which extends for the length of the partition and into which a plurality of longitudinally spaced apart sampling ports extend.

4. A device as claimed in claim 1, in which the or each port seal includes a seal element surrounding one of the ports in the body and the sleeve and sealingly abutting against an opposed surface of the other of the body and the sleeve.

5. A device as claimed in claim 4, in which when the body and sleeve are in their open position the sampling ports are in register and connected in flow communication through the port seal.

6. A device as claimed in claim 1, in which the sleeve has a slot provided therein, a lug attached to the body protrudes through the slot, the open and closed positions of the body and sleeve corresponding to the lug being positioned at opposite ends of the slot.

7. A device as claimed in claim 6, in which the slot extends circumferentially, relative displacement of body and sleeve between their open and closed positions being effected by displacing them angularly relative to one another.

8. A device as claimed in claim 6, in which the slot extends longitudinally, relative displacement of the body and sleeve between their open and closed positions being achieved by relative axial displacement therebetween.

9. A device as claimed in claim 6, in which the slot extends obliquely, relative displacement of the body and the sleeve between their open and closed positions being achieved by relative displacement both angularly and axially.

10. A device as claimed in claim 1, which includes a status display configured to provide a visual indication as to whether the body and sleeve are in their open position or their closed position.

11. A device as claimed in claim 1, which includes an indicator means provided in the body and configured to provide an indication of the presence and nature of contamination in the liquid.

12. A device as claimed in claim 11, in which when the liquid contained in the container is a liquid fuel, the indicator means includes a water indicator element which has a density which is greater than the density of the fuel and less than the density of water.

13. A device as claimed in claim 11, in which the indicator means includes a metal particle indicator comprising a buoyant member, at least part of which is magnetic to attract metal particles contaminating the liquid.

14. A device as claimed in claim 11, in which the indicator means includes a viscosity indicator element.

15. A liquid storage installation which includes
at least one tank in which liquid is receivable; and
at least one device as claimed in claim 1 mounted on the tank to measure and sample liquid contained in the tank.

16. A liquid storage installation as claimed in claim 15, in which the tank is a subterranean tank and the liquid is a liquid fuel.

17. A liquid storage installation as claimed in claim 15, in which the body of the device is provided with markings which when read in conjunction with the level of the liquid in the body provide an indication of the volume of liquid in the tank.

* * * * *